United States Patent [19]
Deigin et al.

[11] Patent Number: 6,051,683
[45] Date of Patent: Apr. 18, 2000

[54] IMMUNE REGULATING PEPTIDES AND METHOD OF OBTAINING THEM

[75] Inventors: Vladislav Isakovich Deigin, North York, Canada; Andrei Marxovich Korotkov, Moscow, Russian Federation

[73] Assignee: Immunotech Developments Inc., Toronto, Canada

[21] Appl. No.: 08/894,963

[22] PCT Filed: Feb. 28, 1996

[86] PCT No.: PCT/RU96/00046

§ 371 Date: Aug. 17, 1998

§ 102(e) Date: Aug. 17, 1998

[87] PCT Pub. No.: WO96/26955

PCT Pub. Date: Sep. 6, 1996

[30] Foreign Application Priority Data

Mar. 2, 1995 [RU] Russian Federation ............ 95102461

[51] Int. Cl.[7] ..................................... A61K 38/04
[52] U.S. Cl. .................. 530/330; 530/330; 530/331; 514/17; 514/18; 514/19
[58] Field of Search .................. 530/330, 331; 514/17, 18, 19

[56] References Cited

U.S. PATENT DOCUMENTS

| | | |
|---|---|---|
| 4,603,121 | 7/1986 | Hansen, Jr. et al. ...................... 514/18 |
| 4,619,916 | 10/1986 | Margonelli et al. . |
| 4,699,897 | 10/1987 | Jones et al. .................................. 514/4 |
| 4,751,216 | 6/1988 | Gottlieb ..................................... 514/18 |
| 4,910,296 | 3/1990 | Birr et al. ............................... 530/324 |
| 5,008,246 | 4/1991 | Schön et al. .............................. 514/18 |
| 5,013,723 | 5/1991 | Sisto et al. ................................. 514/19 |
| 5,070,076 | 12/1991 | Morozov et al. ........................ 514/21 |
| 5,538,951 | 7/1996 | Morozov et al. .......................... 514/19 |
| 5,736,519 | 4/1998 | Deigin et al. ............................. 514/18 |

FOREIGN PATENT DOCUMENTS

| | | |
|---|---|---|
| 29308 | 1/1989 | Australia . |
| 0148133 | 7/1985 | European Pat. Off. . |
| 4014230 | 11/1990 | Germany . |
| 654841 | 3/1986 | Switzerland . |
| 1277903 | 12/1986 | U.S.S.R. . |
| 2100706 | 6/1983 | United Kingdom . |
| WO 92/09628 | 6/1992 | WIPO . |
| WO 93/08815 | 5/1993 | WIPO . |

OTHER PUBLICATIONS

Goldstein et al., *J. Proc. Natl. Acad. Sci. USA*, 74:725,1977.

*Primary Examiner*—F. T. Moezie
*Attorney, Agent, or Firm*—Merchant & Gould P.C.

[57] ABSTRACT

The invention relates to medicine, specifically, to methods of obtaining biologically active substances with immuno-regulating properties, and can be used in medicine and veterinary science and in experimental biochemistry. The fundamental problem addressed by the invention is that of producing a novel synthetic biologically active peptide with immuno-regulating properties and of the formula: X-Glu-Trp-Y, in which X is H or Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, γ-aminobutyric acid, ζ-aminocapronic acid; Y is Gla, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, γ-aminobutyric acid ζ-aminocapronic acid, —OH, $NH_2, N_2H_3$, mono- or di-substituted amide $(C_1-C_3)$. Peptide synthesis takes place in a solution by successive growth of a chain from the C termination of the molecules, using a strategy of maximum blocking of functional groups, starting from amino acid alkyl ether, using the method of activating the ethers and the method of mixed anhydrides using tributyloxicarbonyl amino acid, with the proviso when X is H, Y is not OH.

7 Claims, No Drawings

IMMUNE REGULATING PEPTIDES AND METHOD OF OBTAINING THEM

FIELD OF THE INVENTION

The invention relates to medicine, specifically to methods of obtaining biologically active substances with immuno-regulating properties and can be used in medicine and veterinary science and in experimental biochemistry.

DESCRIPTION OF THE RELATED ART

Thymus extracts are widely used in applied medicine as immuno-regulators, specifically thymozin fraction 5/Goldstein A. L., Guna A., Latz M. M., Hardy H. A., White A./Thymolyn/CH.N 659586/. These extracts are comprised from a Polypeptide culture and their yield from natural sources is limited by the complexity of manufacture. Therefore the yield is not only limited in quantity but also inconsistent in physio-chemical and biological properties. Side effects have been observed in patients who used the polypeptide obtained from natural sources. Due to this, it become obvious for the need for synthetically obtained peptides. In the present time, synthetically synthesised line of peptide is available which possess immuno regulating properties: PCT WO 089/06134, EP N 230052.

U.S. Pat. No. 5,008,246, U.S. Pat. No. 5,013,723. Each synthetically obtained peptide which is limited in essential ingredients is highly active, low in toxicity, void of side effects which make it fit for use in medicine.

SUMMARY OF THE INVENTION

The invention relates to a new biologically active peptide with immuno-regulating properties of the formula X-Glu-Trp-Y, where X is H, Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, γ-aminobuteric acid, or ζ-aminocapronic acid; Y is Gly, Ala, Leu, Ile, Val NVal, Pro, Tyr, Phe, Trp, D-Ala, D-Leu, D-Ile, D-Val, D-NVal, D-Pro, D-Tyr, D-Phe, D-Trp, γ-aminobuteric acid, ζ-aminocapronic acid, —OH, $NH_2$, $N_2H_3$, or a mono- or di-substituted amide ($C_1$–$C_3$); with the proviso that when X is H, Y is not OH.

The invention also relates to a method of making the peptide and to the uses thereof.

DETAILED DESCRIPTION OF THE INVENTION

The question set out to be addressed is that of isolating a new biologically active peptide with immuno-regulating properties.

X-Glu-Trp-Y, where:

X is H or Gly, Ala, Leu, Ile, Val, NVal, Pro, Tyr, Phe, Trp, D-Ala, D-Leu, D-Ile, D-Val, DNVal, D-Pro, D-Tyr, D-Phe, D-Trp, γ-aminobuteric acid, or ζ-aminocapronic acid;

Y is Gla, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, γ-aminobuteric acid, OR ζ-aminocapronic acids, Y is Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, Y-Aminobuteric acid, ζ-aminocapronic acid, —OH, $NH_2$, $N_2H_3$ or di-substituted amide ($C_1$–$C_3$), with the proviso when X is H, Y is not OH.

The goal of the invention was to create a new technological process of creating a peptide. This peptide must be simple to produce and deliver a high quality yield.

The essence of the new method is the synthesis of the new peptide which takes place in a solution by successive growth of a chain from the C termination of the molecules, using a strategy of maximum blocking of functional groups, starting from amino acid alkyl ether, using the method of activating the ethers and the method of mixing anhydrides using tributyloxicarbonyl amino acid.

The peptide chain is outlined in the following table R f1 in (chloroform-methanol-32% acetic acid=60:45:20) and R f2 in (butanol-pyridine-acetic acid=5:5:4:1).

TABLE 1

| PEPTIDE | R f1 | R f2 |
|---|---|---|
| Abu-Glu-Trp-OH | 0.40 | 0.56 |
| Aca-Glu-Trp-OH | 0.41 | 0.57 |
| Ala-Glu-Trp-NH2 | 0.40 | 0.51 |
| Arg-Glu-Trp-OH | 0.26 | 0.48 |
| D-Ala-Glu-Trp-OH | 0.37 | 0.55 |
| D-Ile-Glu-Trp-D-Phe | 0.71 | 0.77 |
| D-Ile-Glu-Trp-OH | 0.39 | 0.54 |
| D-Leu-Glu-Trp-NH2 | 0.35 | 0.56 |
| D-Leu-Glu-Trp-OH | 0.37 | 0.57 |
| D-Val-Glu-Trp-OH | 0.38 | 0.56 |
| D-Phe-Glu-Trp-Ala | 0.69 | 0.76 |
| D-Pro-Glu-Trp-OH | 0.58 | 0.72 |
| D-Trp-Glu-Trp-OH | 0.47 | 0.56 |
| D-Tyr-Glu-Trp-OH | 0.45 | 0.57 |
| D-Val-Glu-Trp-NH2 | 0.43 | 0.53 |
| Gly-Glu-Trp-Gly | 0.44 | 0.49 |
| Gly-Glu-Trp-OH | 0.42 | 0.56 |
| H-Glu-Trp-Abu | 0.49 | 0.54 |
| H-Glu-Trp-Aca | 0.51 | 0.56 |
| H-Glu-Trp-Arg | 0.28 | 0.40 |
| H-Glu-Trp-D-Ala | 0.61 | 0.70 |
| H-Glu-Trp-D-Ile | 0.63 | 0.71 |
| H-Glu-Trp-D-Leu | 0.64 | 0.72 |
| H-Glu-Trp-D-Val | 0.65 | 0.69 |
| H-Glu-Trp-D-Pro | 0.66 | 0.69 |
| H-Glu-Trp-D-Trp | 0.63 | 0.66 |
| H-Glu-Trp-D-Tyr | 0.61 | 0.66 |
| H-Glu-Trp-D-Val | 0.65 | 0.71 |
| H-Glu-Trp-Ile | 0.64 | 0.68 |
| H-Glu-Trp-Gly | 0.54 | 0.58 |
| H-Glu-Trp-NH2 | 0.42 | 0.55 |
| H-Glu-Trp-N2H3 | 0.32 | 0.41 |
| H-Glu-Trp-NVal | 0.67 | 0.71 |
| H-Glu-Trp-Trp | 0.64 | 0.67 |
| H-Glu-Trp-Tyr | 0.62 | 0.66 |
| H-Glu-Trp-Val | 0.66 | 0.71 |
| His-Glu-Trp-OH | 0.31 | 0.58 |
| Ile-Glu-Trp-Phe | 0.71 | 0.78 |
| Ile-Glu-Trp-OH | 0.38 | 0.54 |
| Ile-Glu-Trp-Phe | 0.72 | 0.78 |
| Ile-Glu-Trp-Pro | 0.68 | 0.81 |
| Leu-Glu-Trp-OH | 0.39 | 0.56 |
| Lys-Glu-Trp-OH | 0.30 | 0.51 |
| Lys-Glu-Trp-Tyr | 0.32 | 0.50 |
| NVal-Glu-Trp-OH | 0.37 | 0.55 |
| Phe-Glu-Trp-NH2 | 0.53 | 0.68 |
| Phe-Glu-Trp-Leu | 0.67 | 0.75 |
| Pro-Glu-Trp-OH | 0.59 | 0.72 |
| Trp-Glu-Trp-OH | 0.48 | 0.59 |
| Tyr-Glu-Trp-OH | 0.46 | 0.58 |
| Val-Glu-Trp-Ala | 0.61 | 0.71 |
| Val-Glu-Trp-NH2 | 0.38 | 0.52 |
| Val-Glu-Trp-OH | 0.36 | 0.51 |
| Val-Glu-Trp-Tyr | 0.59 | 0.61 |

The peptide obtained by the above formula has the texture of a white powder, which is soluble in water, not completely soluble in alcohol and non soluble on chloroform.

The Best Way to Obtain the Invention

The invention is illustrated by the following example.

In this example the method of obtaining the peptide is outlined the formula

H-Ile-Glu-Trp-OH.

1. Obtaining Boc-Ile-OPFP

Mixture 46.0 g (0.2 mole) Boc-Ile-OH and 40.5 g (0.22 mole) pentafluorinephenol in 100 ml ethylacetate, chilled to −5° C. and adding 45.3 g (0.22 mle) N,N-dicyclohexylcarbodiimide. The mixture was then stirred in room temperature for three hours, then dicyclohexylcarbamide is filtered out, the solubles are evaporated under vacuum, and the remains are crystallized in a mixture of ethyl acetate-hexane. The residue is then filtered out. The yield–71.3 g (90%).

2. Obtaining Boc-Ile-Glu-Trp-OH 19.8 g (0.05 mole) Boc-Ile-OPFP is dissolved in 100 ml dimethylformamide and while stirring, adding 20 g (0.06 mole) Glu-Trp and 5.0 g (0.06 mole) $NaHCO_3$ dissolved in water. The solution was stirred in room temperature for 20 hours. The solvents where evaporated in vacuum. To the remains was added 200 ml ethyl acetate and 200 ml 2% sulphuric acid while stirring. The organic layer was washed in sulphuric acid (2*100 ml), enriched with NaCl solution to pH=7. Then dried with dehydrated sulphate sodium. The solvents then removed under vacuum. The remains where crystallized in ethyl acetate hexane, the residue was then filtered and dried under vacuum. The yield=20.5 g (75%).

3. Obtaining H-Ile-Glu-Trp-OH 20.5 g BOC-Ile-Glu-Trp-OH was dissolved in 150 ml formic acid, stirring for the duration of 3.5 hours at temperature of 45 C. and the solvent evaporated under vacuum. To the remains, 200 ml water was added and the process of evaporation under vacuum was repeated. To the remains, 300 ml isopropyl and 200 ml ether, was added and left to cure for 10 hours. The remains where filtered and dried under vacuum. The yield=15.3 g (75%).

The purification of the peptide was performed with inverted phase chromatography in acetonitrile 0.1% in a solution of trifluoroacetic acid. The yield 13 g (85%).

After study of the physio chemical properties of the peptide, the following characteristics where discovered:

Initial structure: H-Ile-Glu-Trp-OH

Gross formula: $C_{24}$—$H_{30}$—$N_4$—$O_4$

Molecular weight: BEC-446.5 Da

Visual texture: white powder with a shade of yellow or grey powder.

Solubility—Soluble in water, non soluble in chloroform.

Y,F-spectre in the boundaries of 250–300 mm have maximum 280±2 mm 287±2 mm.

Biological activity of the new peptide was studied on guinea pigs using recognised testing methods of E-yield of lymphocytes of the guinea pigs subsequent to processing with trypsin.

TABLE 2

| Compound | Untreated animals | Treated with trypsin | After treatment with trypsin and compound with concentration mg/ml* | | | | | | |
|---|---|---|---|---|---|---|---|---|---|
| | | | $10^{-6}$ | $10^{-7}$ | $10^{-8}$ | $10^{-9}$ | $10^{-10}$ | $10^{-11}$ | $10^{-12}$ |
| Tymolin | 66.5 | 36.1 | 57.0 | 40.1 | 37.0 | 35.3 | 37.4 | 36.5 | 34.7 |
| Tymozine Fractal 5 | 66.5 | 36.1 | 60.3 | 35.4 | 33.4 | 39.5 | 39.1 | 33.7 | 35.8 |
| Ile-Glu-Trp | 66.5 | 36.1 | 61.4 | 63.9 | 64.8 | 60.2 | 37.5 | 40.0 | 34.3 |

*Each concentration was tested on 5 animals. The positive growth differs in relation to the control group E-POK is 50% or higher.
It is established that in vitro use of the said peptide is active by $10^3$ more then other known compounds.
To establish the safety of use of the peptide, toxicity tests where performed. Toxicity tests where performed according to guidelines and with the cooperation of Pharmacological committee PF "Guidelines for the pre clinical study general toxic activity of new pharmacological compounds". M., 1985.
The results of the experiments showed that with the intervenes injection of 1/1000 dose, the peptide did not exhibit any toxic activity and $LD_{56}$ was not detected.

COMMERCIAL USE

The peptide which possesses biologically active properties can be used in medicine and veterinary science.

We claim:

1. A peptide of the formula I

X-Glu-Trp-Y,  I wherein X is H, Gly, Ala, Leu, Ile, Val, NVal, Pro, Try, Phe, Trp, D-Ala, D-Leu, D-Ile, D-Val, D-NVal, D-Pro, D-Tyr, D-Phe, D-Trp, His, Lys, Arg, γ-aminobutyric acid, or ζ-aminocaproic acid; Y is Gly, Ala, Leu, Ile, Val, NVal, Pro, Tyr, Phe, Trp, D-Ala, D-Leu, D-Ile, D-Val, D-NVal, D-Pro, D-Tyr, D-Phe, D-Trp, Arg, γ-aminobutyric acid, ζ-aminocaproic acid, —OH, $NH_2$, $N_2H_3$, or a mono- or di-substituted amide ($C_1$–$C_3$); with the proviso that when X is H, Y is not OH.

2. A peptide consisting of the sequence H-Ile-Glu-Trp-OH, His-Glu-Trp-OH, H-Glu-Trp-$NH_2$, H-Glu-Trp-Arg, Lys-Glu-Trp-OH, Arg-Glu-Trp-OH, H-Glu-Trp-Tyr, Lys-Glu-Trp-Tyr, H-Glu-Trp-$N_2H_3$, H-Glu-Trp-Gly, or Val-Glu-Trp-OH.

3. A peptide consisting of the sequence H-Ile-Glu-Trp-OH.

4. A pharmaceutical composition comprising at least one peptide of the formula I as claimed in claim 1 and a pharmaceutically acceptable carrier.

5. A method for modulating immune system response of a subject comprising administering to a subject an amount effective for modulating immune system response of a peptide of the formula I as claimed in claim 1 in an amount effective for modulating said immune system response.

6. A pharmacological composition comprising the peptide of claim 3 and the pharmaceutically acceptable carrier.

7. A method for stimulating the immune system of a subject comprising administering to the subject an immune stimulating effective amount of the peptide of claim 3.

* * * * *

UNITED STATES PATENT AND TRADEMARK OFFICE
CERTIFICATE OF CORRECTION

PATENT NO.    : 6,051,683
DATED         : April 18, 2000
INVENTOR(S)   : Deigin et al.

Page 1 of 1

It is certified that error appears in the above-identified patent and that said Letters Patent is hereby corrected as shown below:

Column 4,
Line 47, "Try" should read -- Tyr --

Column 5, claim 5,
Line 2, second instance of "a subject" should read -- the subject -- ( second occurrence)
Lines 2-3, delete "an amount effective for modulating immune system response of"

Signed and Sealed this

Fifth Day of March, 2002

Attest:

Attesting Officer

JAMES E. ROGAN
Director of the United States Patent and Trademark Office